(12) United States Patent
Khan

(10) Patent No.: US 6,309,538 B1
(45) Date of Patent: Oct. 30, 2001

(54) SPA CHEMISTRY MONITORING AND CHEMICAL DISPENSING UNIT

(75) Inventor: Soudy Khan, Palto Alto, CA (US)

(73) Assignee: Polaris Pool Systems, Inc., Vista, CA (US)

( * ) Notice: Subject to any disclaimer, the term of this patent is extended or adjusted under 35 U.S.C. 154(b) by 0 days.

(21) Appl. No.: 09/179,908

(22) Filed: Oct. 27, 1998

(51) Int. Cl.[7] ....................................... B01D 12/00
(52) U.S. Cl. ............................ 210/85; 210/94; 210/96.1; 210/143; 210/198.1; 210/242.1; 422/265; 222/504; 4/496
(58) Field of Search ............................ 210/85, 91, 94, 210/95, 96.1, 143, 169, 198.1, 242.1, 206, 205, 743, 103; 422/261, 263, 265; 222/504; 4/496, 222, 227.1

(56) References Cited

U.S. PATENT DOCUMENTS

| | | | |
|---|---|---|---|
| 3,202,322 | * | 8/1965 | Cleary et al. . |
| 3,677,711 | * | 7/1972 | Bond . |
| 3,746,170 | * | 7/1973 | Bloom et al. . |
| 3,802,606 | * | 4/1974 | Gust . |
| 3,846,078 | * | 11/1974 | Brett . |
| 3,994,420 | * | 11/1976 | Harper et al. . |
| 4,409,980 | * | 10/1983 | Yano et al. . |
| 4,657,670 | * | 4/1987 | Newton . |
| 4,882,072 | * | 11/1989 | Eberhardt . |
| 5,019,250 | | 5/1991 | Lorenzen . |
| 5,097,991 | * | 3/1992 | Lance . |
| 5,167,786 | * | 12/1992 | Eberle . |
| 5,169,236 | * | 12/1992 | lest . |
| 5,407,567 | * | 4/1995 | Newhard . |
| 5,795,511 | * | 8/1998 | Powell . |
| 5,932,093 | * | 8/1999 | Chulick . |
| 5,933,575 | * | 8/1999 | Sanders . |

\* cited by examiner

Primary Examiner—Matthew O. Savage
Assistant Examiner—Terry Cecil
(74) Attorney, Agent, or Firm—Kelly Bauersfeld Lowry & Kelley, LLP

(57) ABSTRACT

A self-contained and free floating spa chemistry monitoring and dispensing unit is provided for automated checking and adjusting of water chemistry in a spa tub or the like to maintain the spa water in a clean and substantially sanitary state. The unit includes a compact bouyant housing having an on-board controller coupled to a plurality of sensor electrodes in contact with the water. The controller is programmable to cause the sensor electrodes to take water chemistry readings at predetermined time intervals in order to determine, for example, the pH or the oxidation reduction potential of the spa water. A dispensing means is operated by the controller to dispense chemicals to the water in an amount responsive to the water chemistry readings. The dispensing means includes metering assemblies mounted within the necks of bottles, wherein each bottle contains a respective chemical for affecting spa water chemistry. The housing includes a plurality of upwardly open sockets for removably supporting the bottles in an inverted position. The sockets include a cooperative means for receiving a unique one of the bottles.

33 Claims, 15 Drawing Sheets

SPA CHEMISTRY MONITORING AND CHEMICAL DISPENSING UNIT

BACKGROUND OF THE INVENTION

This invention relates generally to devices and methods for monitoring and regulating the water chemistry in a spa or hot tub or the like, to maintain the water quality at a clean, clear, and substantially sanitary condition. More specifically, this invention relates to a self-contained and free floating monitor unit for checking selected water chemistry parameters at programmable intervals, and for automatically responding to the monitored parameters by delivering one or more chemical additives to the water to maintain the spa water in a clean and hygienic state.

Therapeutic spas and hot tubs and the like are generally known in the art, and typically comprise an upwardly open structure adapted to contain a selected volume of water. Control means are normally provided for heating the water, and for circulating the water through air-water hydrotherapeutic massage jets. One or more persons can sit within the spa, partially immersed within the heated water, in positions so that the spa jets can be directed against the body to provide a therapeutic massage action. To maintain the spa water in a clean and sanitary condition, the circulating water is normally passed through a filter which removes and collects particulate matter. In addition, selected chemical agents such as chlorine are periodically added to the spa water in prescribed amounts suitable for preventing growth of bacterial organisms, to maintain the water in a hygienic state. Other chemical agents such as a sanitizer, e.g., an oxidizer such as bromine, are also periodically added to the water.

In the past, periodic manual testing of the spa water has been required to determine the actual concentration of chemical agents therein, in order to determine whether one or more chemical agents should be added to the spa water to maintain a desired sanitary condition. In this regard, the pH level (a logarithmic function of hydrogen ion concentration) is commonly checked by the spa owner or by maintenance personnel at regular intervals, and chemical agents such as a selected base or acid are added to the water in appropriate amounts for respectively adjusting the pH level up or down as may be required to maintain the pH reading within a typical desired range of about 7.2–7.8. In addition, oxidation reduction potential (ORP) is also checked regularly, and a selected chemical sanitizer such as bromine is added to the water in an appropriate amount to maintain the ORP reading within a typical desired range of about 650–750 millivolts when the pH reading is within the above-stated desired range. Regular monitoring of the water chemistry, and regular addition of these chemical agents in the appropriate amounts, is essential to maintain the spa water in a clean and sanitary condition. However, manually conducted water chemistry testing and manual addition of the chemical agents has been highly subject to time interval variations and measurement inconsistencies which can have an adverse impact upon water quality.

For some swimming pool and spa installations, devices and systems have been developed for unattended delivery of certain chemical agents to the water over an extended period of time. For example, floating dispensers have been widely used in swimming pool and spa applications, wherein a quantity of a chemical such as chlorine or bromine is carried by a buoyant housing which has a variably opened gate for controlled release of the chemical on a substantially continuous basis and for an extended period of time. In such dispensers, the floating housing typically carries a supply of chemical-containing tablets in solid form, designed for rate-controlled dissolution according to the degree to which the gate is opened. While such dispensers beneficially maintain the chemical concentration, the delivery rate is still predicated upon periodic manual water chemistry testing and corresponding periodic gate adjustment to regulate the chemical delivery rate. Moreover, such floating dispensers have not been designed to accommodate delivery of other chemical agents, such as acids or the like when a reduction in pH level is indicated, or a sanitizer or oxidizer for regulating and maintaining the ORP level within a prescribed reading range. The need for and the addition of such other chemical agents has still relied upon periodic manual water chemistry testing and periodic manual addition of the chemical agents in selected amounts to the pool or spa water.

In other swimming pool and spa installations, substantially automated systems have been designed for integration in-line into the water filtration and circulation equipment for automatically analyzing the water chemistry at periodic intervals, and for responding to the chemistry readings to automatically add chemical agents to the water in prescribed amounts. See, for example, the automated pool water chemistry marketed by Polaris Pool Systems of San Marcos, California under the product designation Watermatic. See also U.S. Pat. No. 5,019,250. Such automated systems, however, are relatively complex and are thus relatively costly, particularly with respect to the requisite plumbing modifications for installation into the filtration system of a pre-existing pool or spa. Moreover, the complexity and resultant cost of such automated in-line chemical dispensers has been a significant deterrent to use thereof in stand-alone spas which do not share a water filtration system with an associated swimming pool. Accordingly, such automated chemical dispenser systems have not been widely used.

The present invention overcomes these problems and disadvantages by providing a compact and self-contained floater device for automatically analyzing spa water chemistry at regular programmable intervals, and for automatically responding to the water chemistry readings to add one or more chemical agents in appropriate amounts to maintain the spa water in clean and highly sanitary state.

SUMMARY OF THE INVENTION

In accordance with the invention, a water chemistry monitor unit is provided for automated monitoring and regulation of the water chemistry in a spa tub or hot tub or the like, to maintain the water in a clean and sanitary condition. The monitor unit comprises a relatively compact buoyant housing adapted to float freely within the spa water. The monitor unit includes a programmable controller coupled to one or more sensor electrodes for monitoring selected water chemistry parameters at timed intervals. The monitor unit responds to the parameter readings to deliver one or more chemical agents in appropriate amounts to maintain the monitored parameters within prescribed ranges consistent with maintaining the water in a clean and sanitary condition.

In the preferred form, the controller is mounted on-board within the housing of the monitor unit, and an exposed data entry panel is provided for programming the controller to activate the sensor electrodes at predetermined clock times to take readings of the water chemistry parameters. In the preferred form, the sensor electrodes are designed for reading the hydrogen ion concentration level (pH), and for reading oxidation reduction potential (ORP). The controller responds to the pH level reading to deliver an appropriate amount of a selected chemical agent such as a selected base, e.g., sodium carbonate to raise the pH level, or alternately to deliver an appropriate amount of a selected chemical agent such as muriatic acid or other selected acid solution to lower the pH level, for the purpose of maintaining the pH level of the spa water within a predetermined range typically on the order of about 7.2–7.8. In addition, the controller responds to the ORP reading to deliver a selected chemical agent such as a sanitizer or oxidizer, e.g., bromine, to maintain the ORP level of the spa water within a predetermined range typically on the order of about 650–750 millivolts when the pH level is within the above-stated prescribed range.

The chemical agents are carried by the housing of the monitor unit and appropriate amounts thereof are delivered automatically under regulation by the controller, in response to the monitored parameter readings. More particularly, in the preferred form, separate chemical agents such as a base and an acid in liquid form for respectively adjusting the pH level up or down are contained within individual and preferably prepackaged containers or bottles adapted for mounting in an inverted position within individual and uniquely matingly shaped sockets formed in the unit housing. In the preferred form, an additional or third chemical agent in liquid form such as a strong oxidizer or shock agent or the like, typically a strong chlorine solution, may also be provided within an individual bottle for inverted mounting into a matingly shaped socket on the unit housing. These bottles each include a metering assembly mounted in the neck thereof for engaging an associated plunger of a solenoid actuator mounted on the housing of the monitor unit. In operation, in programmed response to the water chemistry readings, the controller actuates one or more of the solenoid actuators to displace the associated plungers through a selected number of advance and retract strokes, to deliver an appropriate number of discrete doses of the appropriate chemical agent or agents to the spa water.

In addition, in accordance with the preferred form, the chemical agent for regulating ORP level is provided in solid form such as soluble tablets or the like contained within a cartridge suspended from the housing of the monitor unit. The cartridge includes a perforated segment positioned in underlying relation to a rotary gate of perforated construction, wherein the rotary gate is movably positioned by the one or more solenoid actuators in accordance with the detected ORP level to permit or prevent spa water circulation into contact with the soluble tablets in the cartridge. In this manner the perforated segment on the cartridge can be opened or closed to control tablet dissolution and thereby regulate delivery of the associated chemical agent to the spa water. Alternately, the solenoid actuator may be movably positioned for variably opening and closing the perforated segment on the cartridge to variably adjust the rate of chemical addition in response to the ORP reading.

Other features and advantages of the present invention will become more apparent from the following detailed description taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
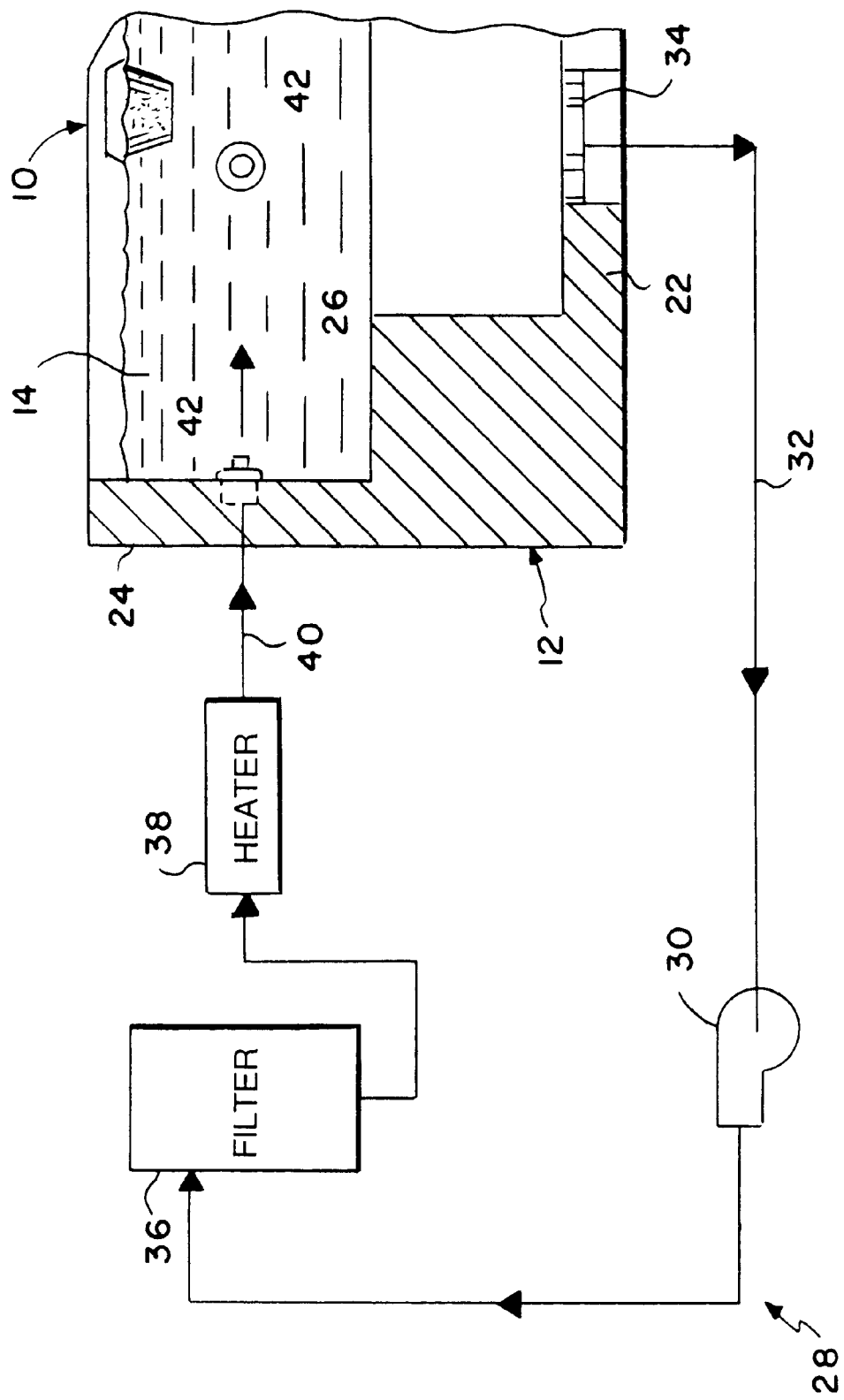
FIG. 1 is a schematic illustration depicting a typical spa or hot tub installation including a spa water circulation and filtration system, with a spa chemistry monitor unit embodying the novel features of the invention shown floating in the spa water.

As shown in the exemplary drawings, a spa chemistry monitor unit referred to generally in FIG. 1 by the reference numeral 10 is provided for automatic or unattended monitoring of water chemistry parameters in a spa or hot tub 12 or the like, and for automatic or unattended dispensing of one or more chemical agents in appropriate amounts in response to parameter readings. The monitor unit 10 generally comprises a compact and free floating device adapted for simple placement into the spa water 14. The monitor unit 10 includes an on-board controller 16 (FIG. 4) which is programmable to take specific water chemistry parameter readings at predetermined regular times by electronic activation of a pair of sensor electrodes 18 and 20 (FIGS. 4 and 5) disposed in direct contact with the spa water 14. In response to these parameter readings, the controller 16 automatically dispenses one or more specific chemical agents carried by the monitor unit, in a dosage amount or rate of flow to maintain the spa water in a substantially optimized condition of clarity and hygiene.

The spa chemistry monitor unit 10 of the present invention is designed for substantially automated water quality monitoring and maintenance in a body of water such as a typical spa or hot tub 12 or the like. In this regard, the spa or hot tub 12 is depicted generally in FIG. 1 to comprise an upwardly open structure including a floor 22 joined to a surrounding and upstanding side wall 24 for containing the spa water 14. The spa 12 is typically sized to accommodate one or more persons (not shown) in a partially immersed position, commonly to include a bench or seat 26 to allow such person or persons to sit comfortably within the water. A filtration system 28 is also normally provided to include a pump 30 for drawing water through a suction conduit 32 from one or more drains 34, and for circulating such water through a filter canister 36 and a heater 38 prior to return flow to the spa 10 via one or more return conduits 40. As is known in the art, the filter canister 36 includes a suitable filtration medium (not shown) for capturing and separating particulate from the spa water, whereas the heater 38 is designed to elevate the water temperature to a level typically in the range of about 95–105° F. The filtered and heated spa water 12 is normally recycled to the spa 10 through one or more hydrotherapy massage jet nozzles 42 mounted at spaced locations on the side wall 24 beneath the water line, wherein these massage jet nozzles 42 may also include means (not shown) for entraining air bubbles into the water stream to provide a vigorous air-water massage action.

The spa chemistry monitor unit 10 comprises a compact and free floating device for simple drop-in placement into the spa water 14, as viewed in FIG. 1. The monitor unit 10 is programmable for automatic or unattended operation to analyze the spa water chemistry on a regular basis, and to add specific chemical agents to the spa water in response to the actual water chemistry readings for the purpose of maintaining the water in a clean, clear and hygienic state. These chemical agents are carried in prepackaged containers mounted directly on the monitor unit 10 for appropriate engagement with actuator means to deliver the correct chemical agent or agents each in the correct dosage amount to maintain spa water quality.

Figure 2:
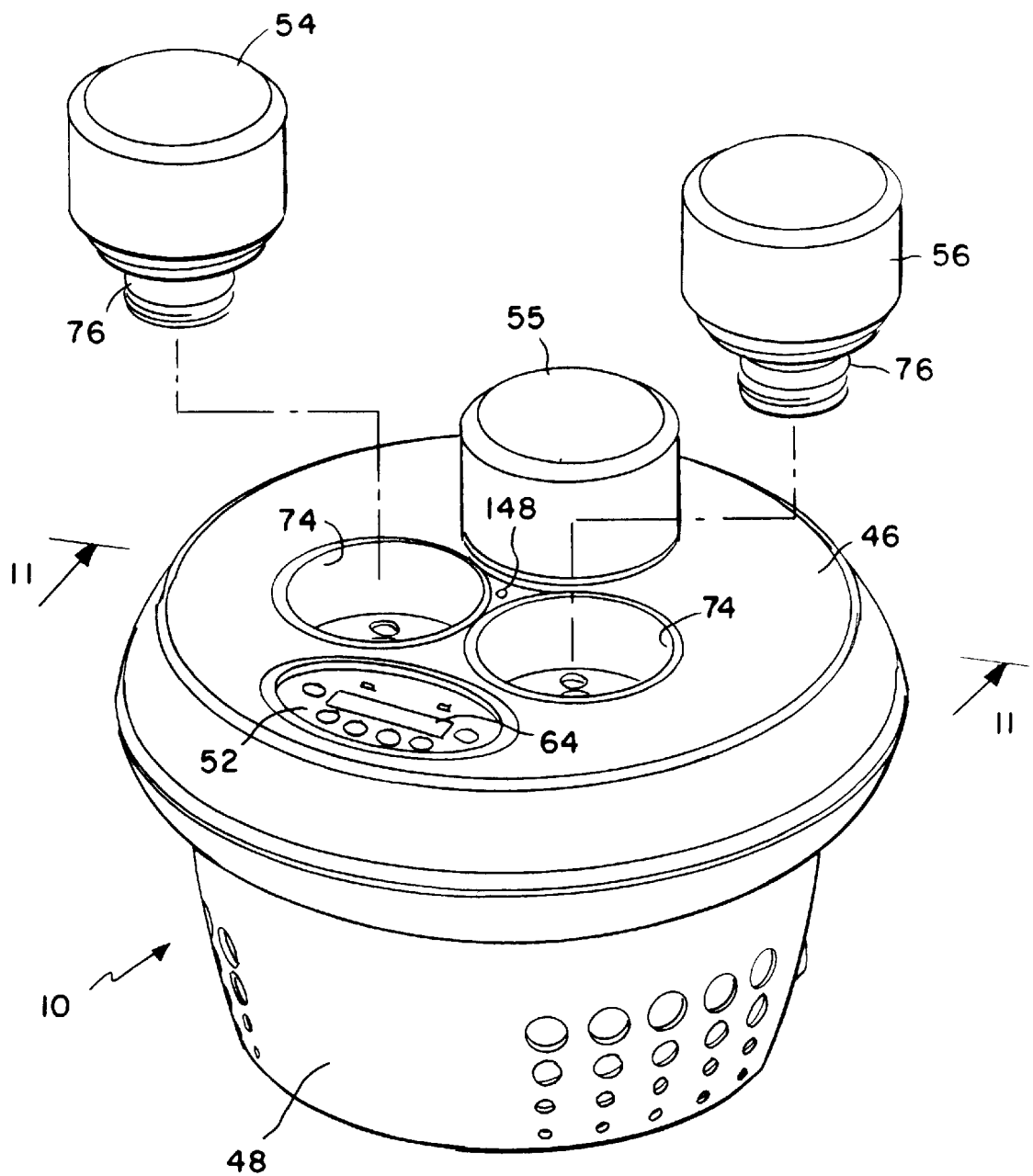
FIG. 2 is an enlarged perspective view, shown partially in exploded form, illustrating the top and one side of the spa chemistry monitor unit shown in FIG. 1.
Figure 3:
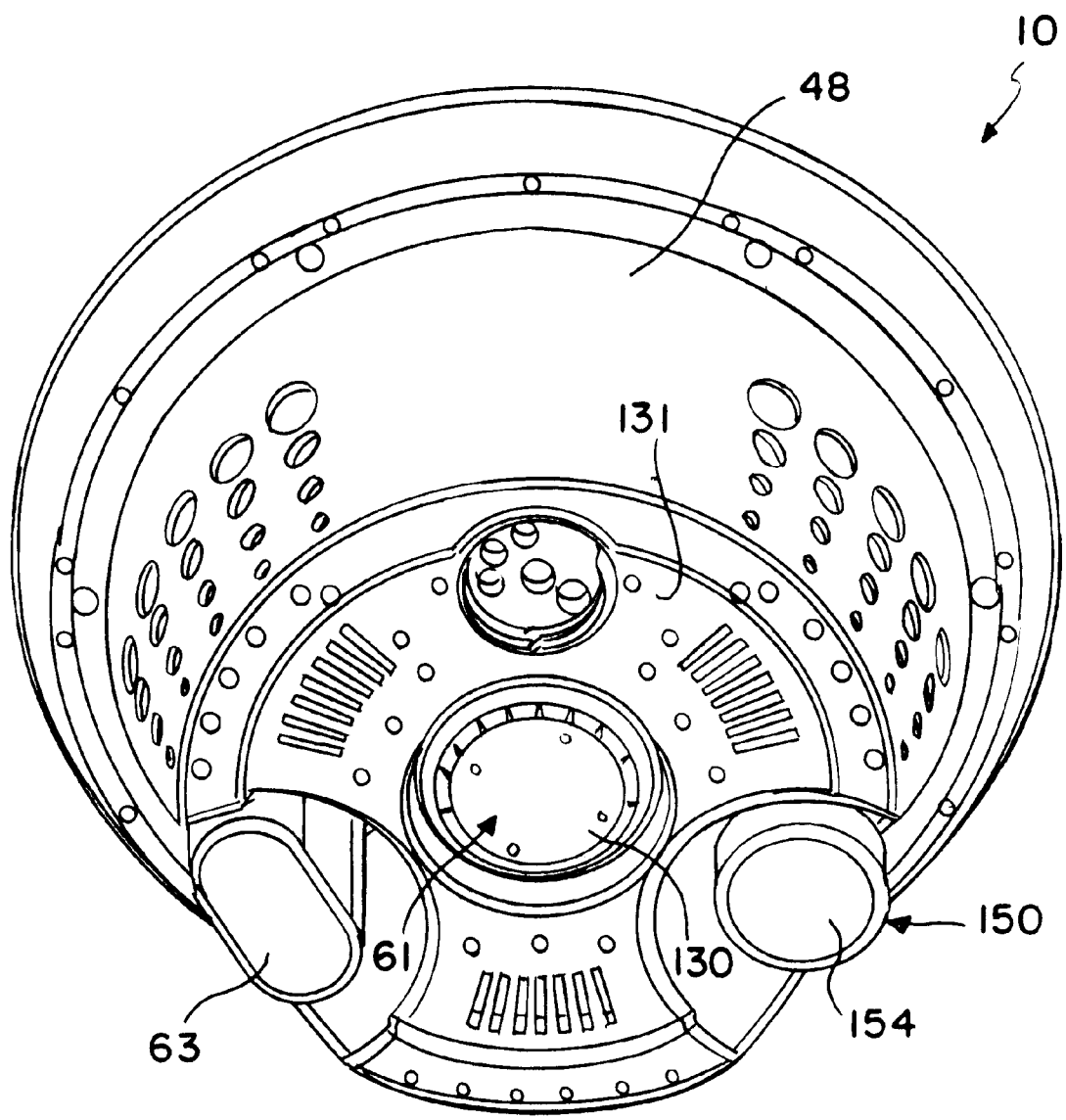
FIG. 3 is a bottom perspective view of the monitor unit.
Figure 4:
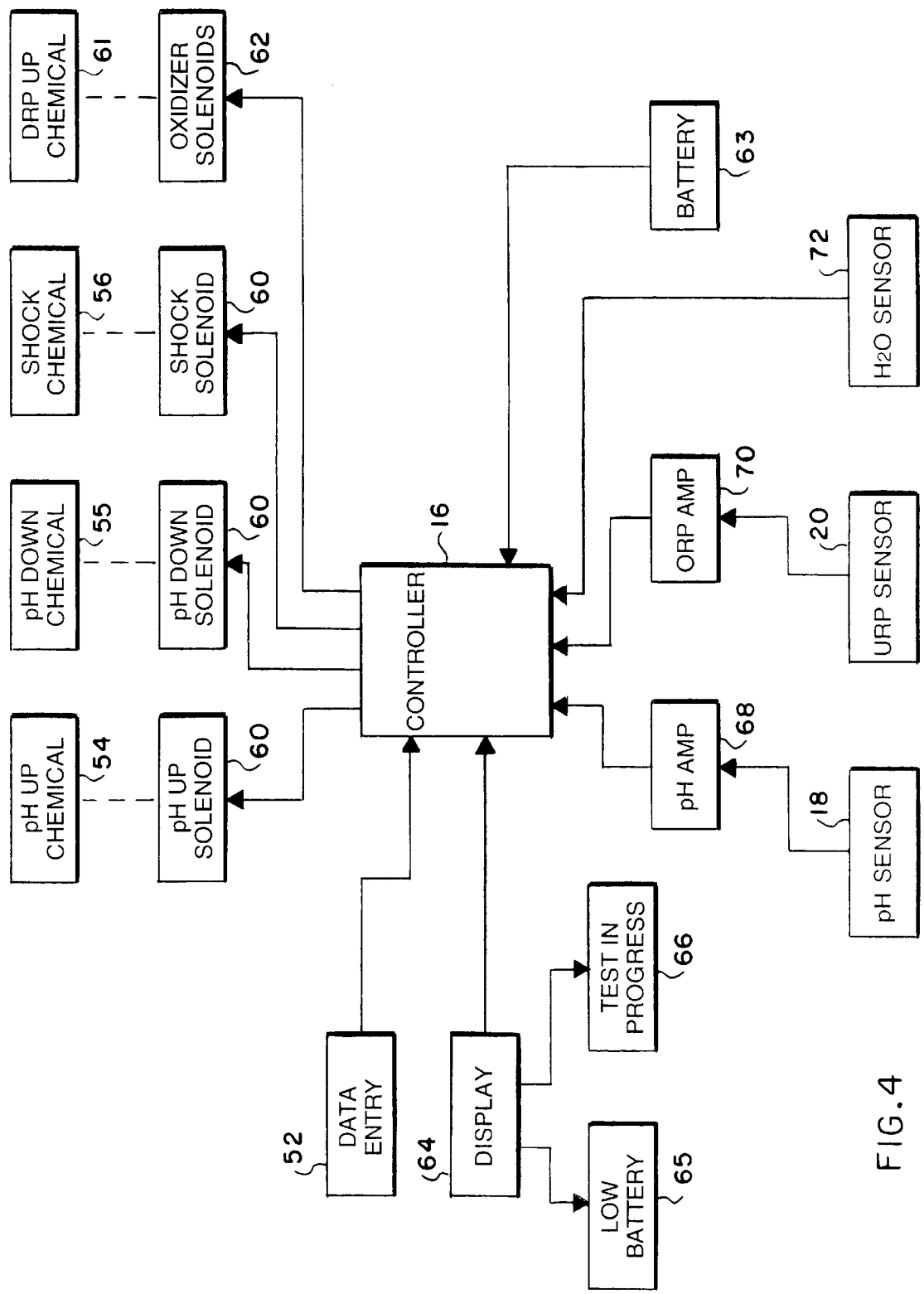
FIG. 4 is a schematic diagram illustrating programmable operation of the monitor unit.
Figure 5:
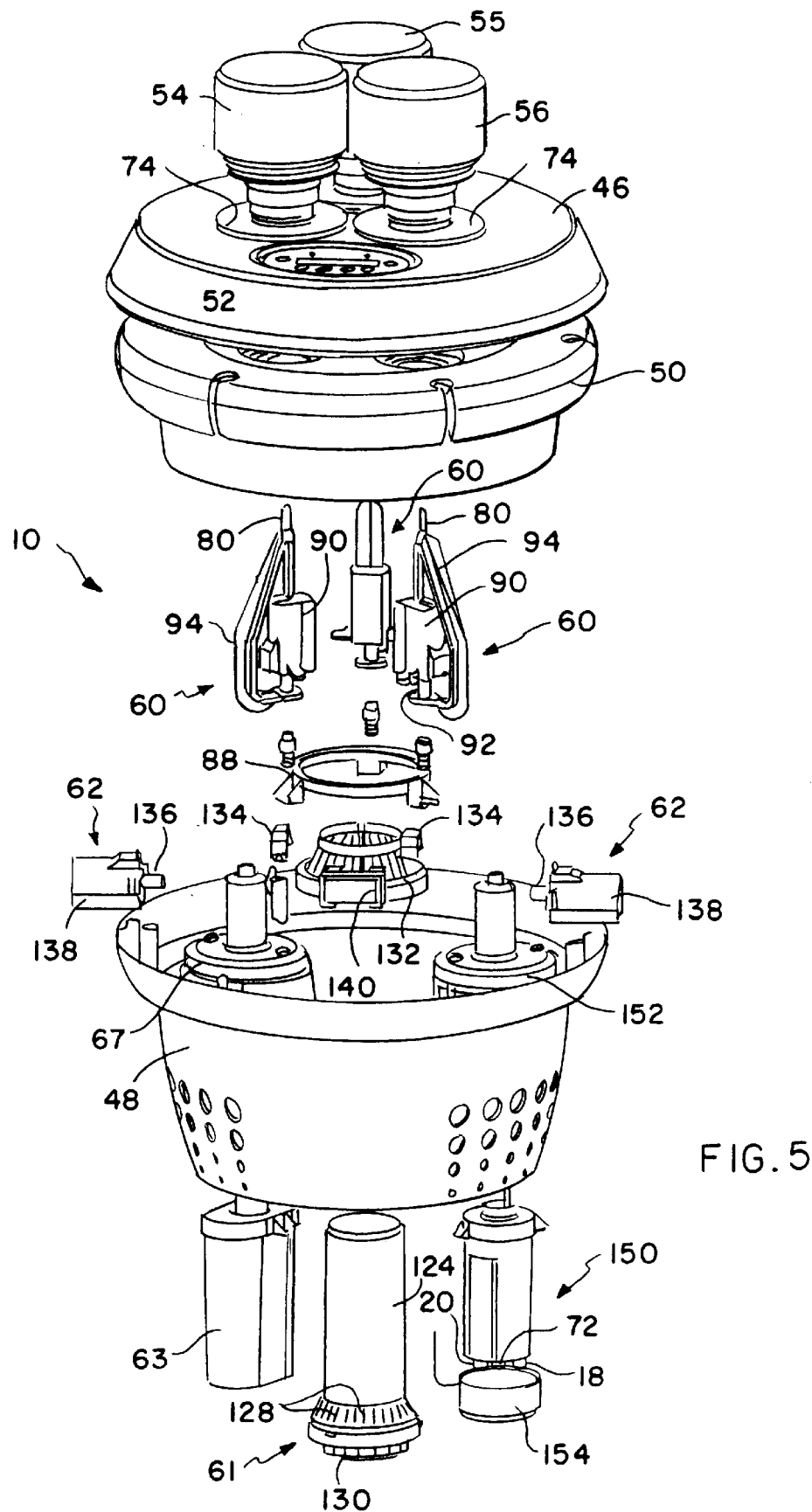
FIG. 5 is an exploded perspective view of the monitor unit.
Figure 6:
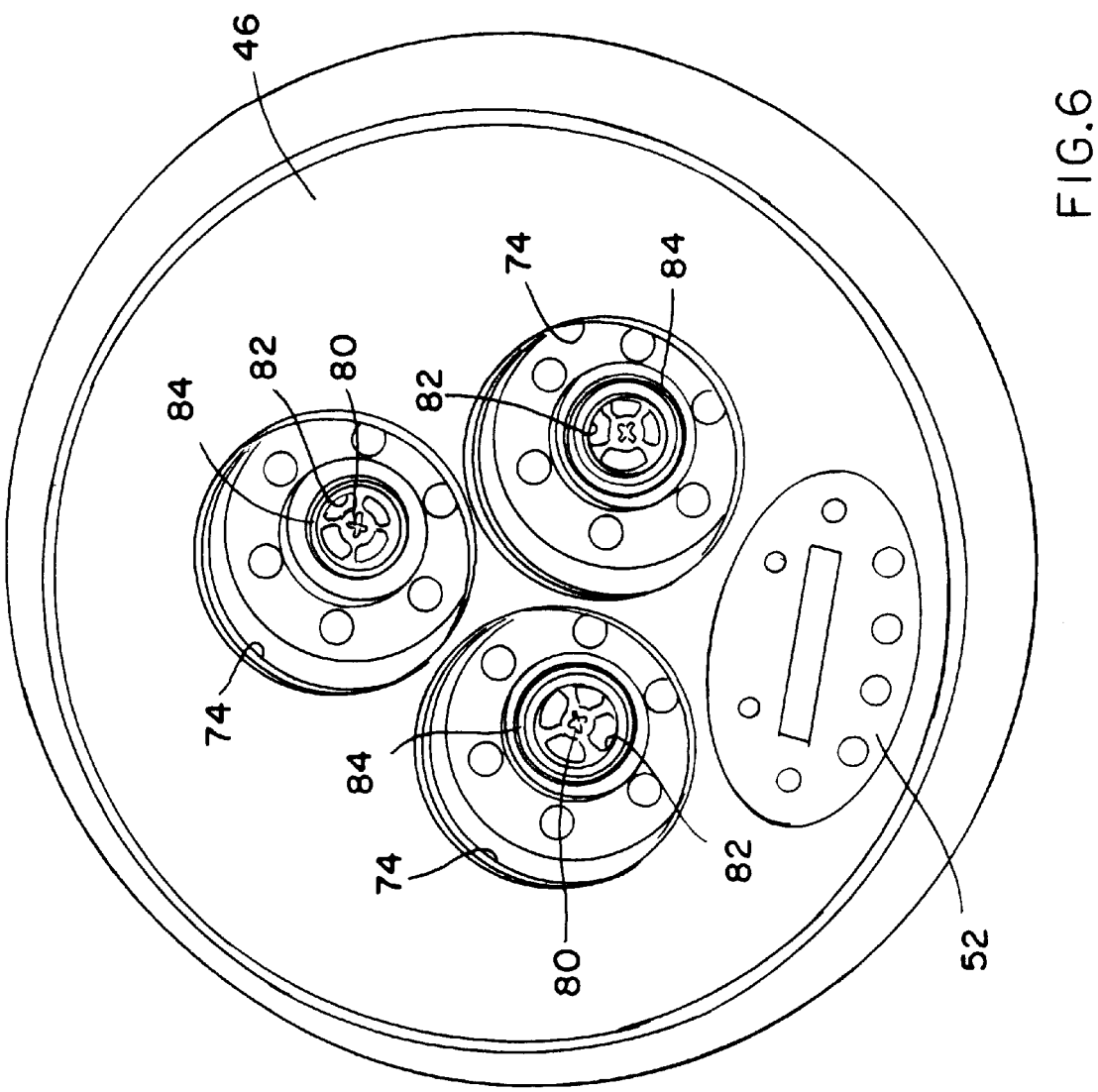
FIG. 6 is a top plan view of the monitor unit, with chemical agent containers removed therefrom to illustrate mounting sockets for receiving and supporting said containers.
Figure 7:
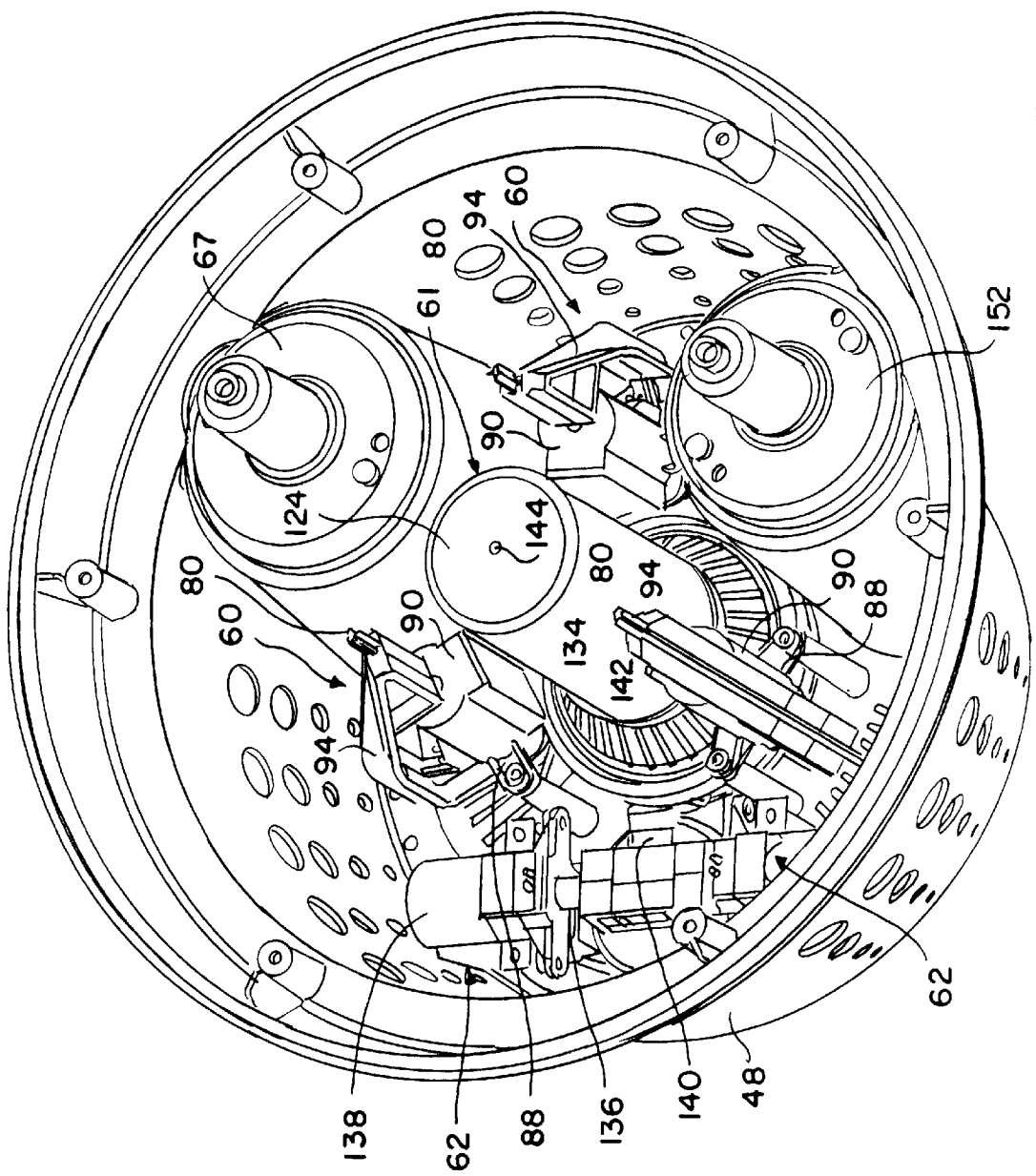
FIG. 7 is a perspective view of a portion of the monitor unit, with an upper portion of the monitor unit removed to reveal internal components thereof.
Figure 8:
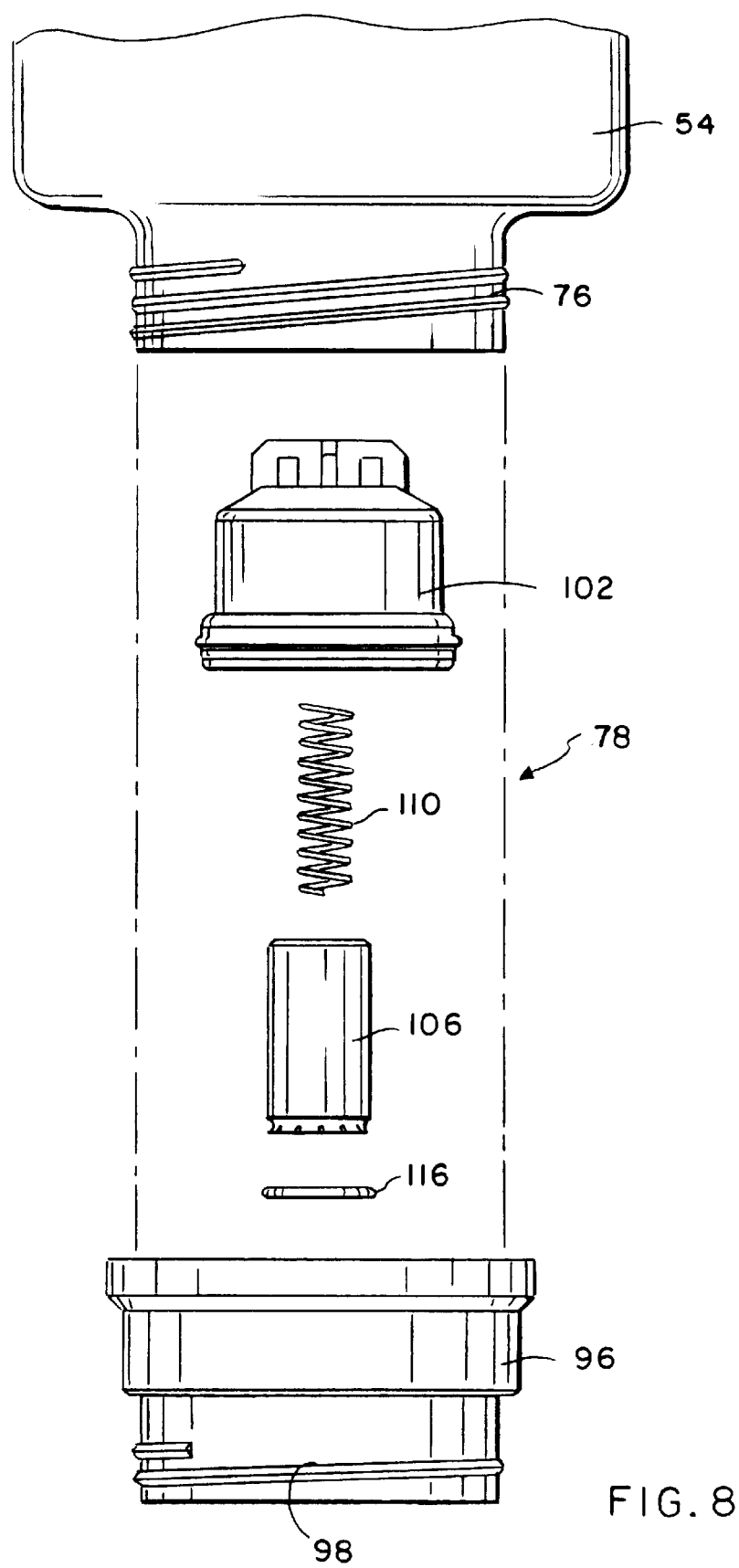
FIG. 8 is an exploded and partially fragmented side elevational view of a portion of a chemical agent container, depicting components of a metering assembly mounted in a neck of the container.
Figure 9:
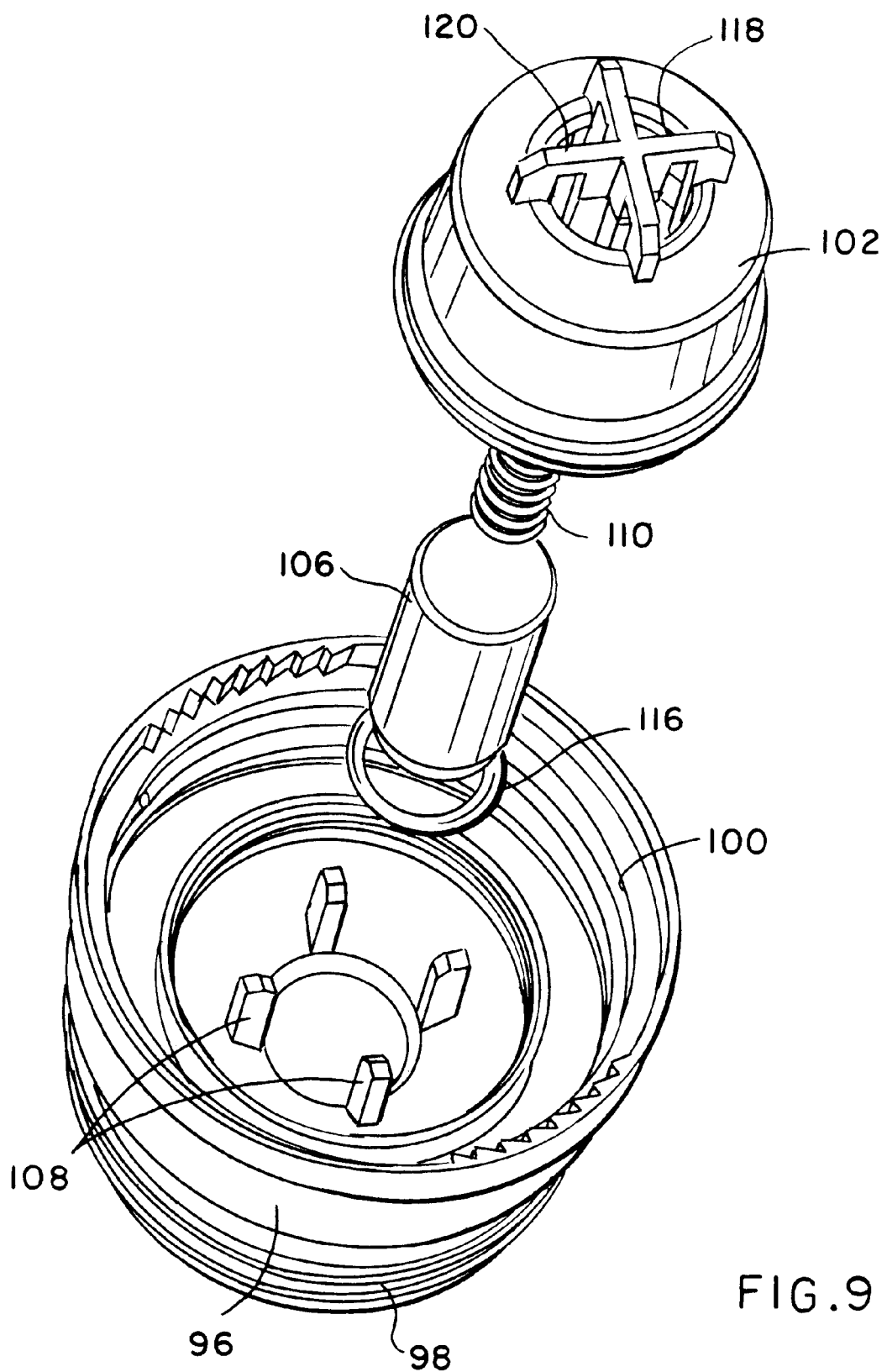
FIG. 9 is an exploded perspective view further illustrating components of the metering assembly from an inboard side thereof.
Figure 10:
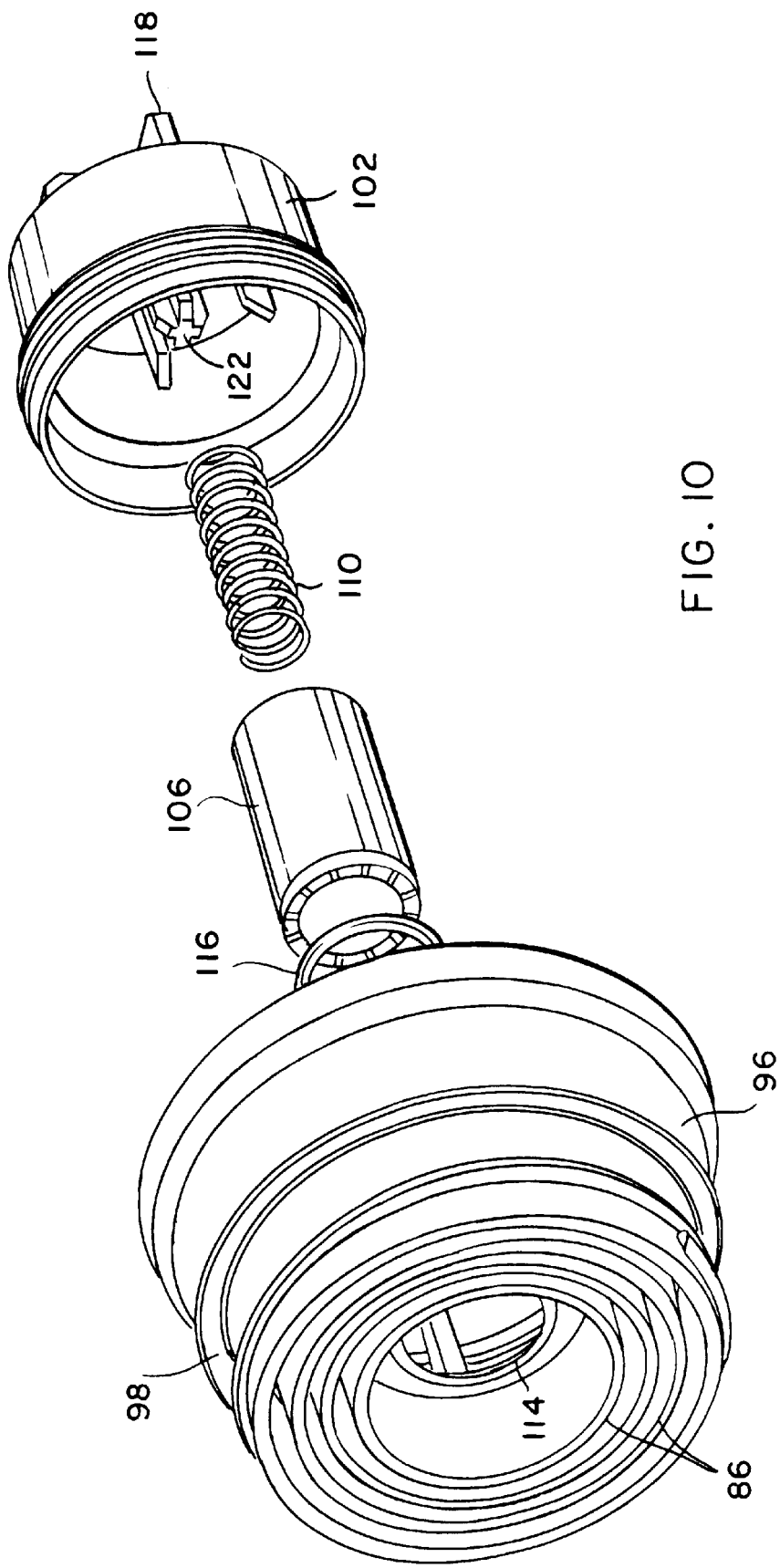
FIG. 10 is an exploded perspective view further illustrating components of the metering assembly from an outboard side thereof.

As shown generally in FIGS. 2–3 and 5, the monitor unit 10 comprises a main housing constructed from molded plastic or the like to include an upper housing plate 46 attached by screws or the like (not shown) to a lower housing base 48 in a manner capturing and retaining therebetween a buoyant float ring 50 (FIG. 5) of expanded foam material or the like. The upper housing plate 46 carries an upwardly exposed data entry panel or keyboard 52 to enable programming of the controller 16 (FIG. 4) for automated operation to take water chemistry readings. The upper housing plate 46 also supports a plurality of pre-packaged chemical agent containers, three of which are shown in the illustrative drawings in the form of inverted liquid-containing bottles 54, 55 and 56. Each of these chemical agent bottles 54–56 carries a metering assembly 78 (FIGS. 8–10) in the mouth-forming neck thereof for engagement by an associated solenoid actuator 60 (FIGS. 5, 7 and 11–12) mounted on the housing base 48 to dispense the chemical agent in metered doses, all under the control of the controller 16. An additional chemical agent in solid soluble form is carried within a cartridge 61 (FIGS. 7 and 13–15) mounted removably on the housing base 48 for engagement with a pair of solenoid actuators 62 to regulate contact of the soluble chemical agent with the spa water. A battery power pack 63 (FIGS. 3 and 5) is removably suspended from a battery terminal fixture 67 on the housing base 48 to provide a safe source of electrical power to operate the monitor unit 10. The lower housing base 48 is perforated to permit spa water circulatory flow into and through the interior of said lower housing base.

The monitor unit 10 is depicted in schematic form in FIG. 4. More particularly, the monitor unit 10 includes the controller 16 in the form of a microcontroller such as a small computer or computer chip powered by the battery pack 63. The controller is coupled to the data entry panel 52 which includes appropriate keys (FIG. 2) for entering programming information. Specifically, the data entry panel 52 is utilized to enter information such as time of day, spa size in gallons of water, and a schedule for taking water chemistry readings. In addition, the data entry panel 52 may be used to program the target ranges for water chemistry readings together with associated chemical agent dosages to be added to the spa water in response to water chemistry readings, although such information may be pre-programmed into the controller 16 in the form of a "read only" memory. A visual display 64 such as a liquid crystal display (LCD) is associated with the data entry panel 52 and may include appropriate alpha-numeric characters for facilitated data entry. In the preferred form, the visual display 64 also includes indicators to indicate the operational state of the monitor unit 10, such as an indicator 65 reflecting low battery pack power, and an indicator 66 reflecting that a water chemistry reading test is in progress.

Water chemistry readings are taken at programmed intervals by the monitor unit 10, by means of the pair of sensor electrodes 18 and 20. In the preferred form of the invention, the sensor electrode 18 is designed for reading the hydrogen ion concentration level of the spa water, normally expressed as a logarithmic function in the form of pH level. By contrast, the second sensor electrode 20 is designed for reading the oxidation reduction potential (ORP) of the spa water. These two sensor electrodes 18, 20 are coupled via a corresponding pair of amplifiers 68 and 70 to the controller 16. As described above, the controller 16 is programmed to activate the sensor electrodes 18, 20 at predetermined times to take these water chemistry readings.

The controller 16 responds automatically to the detected water chemistry levels to deliver chemical agents in appropriate amounts to maintain the water chemistry levels within preselected reading ranges consistent with clear and sanitary water conditions. In this regard, a typical preferred pH level is in the range of about 7.2 to about 7.8. If the water chemistry reading reveals an actual pH level below this range, one of the solenoid actuators 60 is activated by the controller 16 to dispense a chemical agent such as a base solution (e.g., sodium carbonate) from the first bottle 54, in one or more metered doses sufficient to adjust the pH level upwardly to within the prescribed range. Alternately, if the chemistry reading indicates an actual pH level above the prescribed range, a second one of the solenoid actuators 60 is activated by the controller 16 to dispense a second chemical agent such as a selected acid solution or the like (e.g., muriatic acid) from the second bottle 55, again in an amount appropriate to adjust the pH level back to within the prescribed range. In the same general manner, if the ORP water chemistry reading indicates that the actual ORP level is below a typical preferred range of about 650–750 millivolts which is reflective of the parts-per-million (ppm) concentration of the sanitizing agent, the set of solenoid actuators 62 are appropriately activated by the controller 16 to open the cartridge 61 for ingress of spa water to dissolve the soluble chemical sanitizing agent (e.g., bromine tablets)

contained therein. Conversely, if the actual detected ORP level is within or above the prescribed range, the solenoid actuators 62 are movably positioned by the controller 16 to close the cartridge 61 and thereby prevent further addition of the soluble chemical sanitizing agent to the spa water. In this regard, the ORP level reading is generally dependent upon the pH level which needs to be within the prescribed range as noted above, to obtain ORP readings which reliably indicate the need to dispense the sanitizing agent.

In the illustrative preferred form of the invention, the third liquid-containing chemical agent bottle 56 may carry an oxidizer or so-called shock chemical which is added to the spa water 14 in a selected amount at periodic, relatively long-term programmable intervals such as weekly in accordance with spa usage. The controller 16 is programmed to activate the solenoid actuator 60 associated with the bottle 56 at the programmed time to deliver the shock agent in the prescribed dose to the spa water. A typical shock agent for this purpose comprises a strong chlorine solution. In addition, or in the alternative, the controller 16 may be programmed to accommodate manually initiated addition of the shock chemical to the water upon appropriate manipulation of the data entry panel 52.

Since the monitor unit 10 of the present invention is normally intended to be removed from the spa 12 when the spa is being used by one or more persons, a water sensor electrode 72 is also provided in the system. This water sensor electrode 72 is designed to detect whether the monitor unit 10 is floating within the spa water 14, or whether the monitor unit has been temporarily removed from the spa. If the monitor unit is in the spa, the water sensor electrode 72 signals the controller 16 to proceed with water chemistry readings and appropriate additions of chemical agents in a normal manner. However, if the water sensor electrode 72 detects that the monitor unit has been removed from the spa, the controller 16 is signaled to postpone water chemistry readings and chemical agent additions until the monitor unit is again returned to the spa, as detected by the water sensor electrode 72.

As shown in FIGS. 2–3, and 5–6, the upper housing plate 46 of the monitor unit 10 includes a plurality of upwardly open and relatively shallow cup-shaped sockets 74 having a size and shape for respectively receiving and supporting the chemical agent bottles 54–56 in an inverted orientation. In this regard, in the illustrative preferred embodiment of the invention, three of these sockets 74 are provided in the upper housing plate 46 in a generally triangular array for substantially mated fit reception of the mouth-forming necks 76 of the chemical agent bottles 54–56, wherein each bottle neck 76 incorporates a metering assembly 78 (FIGS. 8–12) for dispensing the associated chemical agent in discrete doses of predetermined measured volume to the surrounding spa water 14. The metering assembly 78 is operated by a solenoid plunger tip or pin 80 forming a portion of the associated solenoid actuator 60 mounted on the lower housing base 48 (FIGS. 5, 7 and 11–12), with the plunger tip 80 protruding upwardly through a central port 82 formed within the bottom of the associated socket 74.

In accordance with one aspect of the invention, each socket 74 further includes an array of ribs 84 in the bottom thereof (FIG. 6) for uniquely interfitting with matingly shaped ribs 86 (FIG. 10) on the associated chemical agent bottle. With this construction, each of the three chemical agent bottles 54–56 is adapted for respective cooperative or complementary installation into a specific and unique one of the three sockets 74. In other words, the first bottle 54 containing, for example, a base solution for use in raising the pH level of the spa water, is adapted to fit only within a single one of the sockets 74, such as the socket associated in FIGS. 2 and 6 by the adjacent Roman numeral legend "I" on the upper housing plate 46. Similarly, the second bottle 55 containing an acid solution for use in lowering water pH level is adapted to fit only within a single one of the sockets, such as the socket associated in FIGS. 2 and 6 with the Roman numeral legend "II". Finally, the third bottle 56 containing, for example, a selected shock solution is adapted to fit only within the remaining socket 74 identified in FIGS. 2 and 6 with the Roman numeral legend "III". The controller 16 is pre-programmed to recognize the association of these individual sockets 74 with specific chemical agents to be dispensed to the spa water. The uniquely and matingly shaped interfit between the ribs 86 of the bottle necks 76 and the associated ribs 84 within the sockets 74 prevents undesirable loading of a socket 74 with a bottle containing the incorrect chemical agent.

The solenoid actuators 60 associated with the chemical agent bottles 54–56 are shown best in FIGS. 5, 7 and 11–12. As shown, three such solenoid actuators 60 are provided on a mounting bracket 88 (FIG. 5) secured in a suitable manner to the lower housing base 48. Each solenoid actuator comprises an armature 90 actuatable by the controller 16 to advance and retract a downwardly projecting core pin 92. More particularly, when the armature 90 is energized, the core pin 92 is retracted upwardly into the armature 90, whereas upon armature de-energization the core pin 92 returns to a normal downwardly extending position. The core pin 92 carries a plunger arm 94 which projects upwardly around the associated armature 90 and terminates at its upper end in the plunger tip 80 received through the central port 82 in the associated socket 74, as previously described. Reciprocal motion of the core pin 92 within the armature 90 serves to reciprocate the plunger tip 80 through advance and retract strokes to operate the metering assembly 78 on a chemical agent bottle installed into the socket 74.

The metering assembly 78 is shown in detail in FIGS. 8–12 with respect to the chemical agent bottle 54, with the understanding that each chemical agent bottle 54–56 is equipped with a metering assembly 78 of the same or functionally similar construction. As shown, the metering assembly 78 comprises an outer cap 96 mounted as by threading onto the bottle neck 76, wherein the outer cap further defines an external thread segment 98 which cooperates with the associated unique ribs 84 for unique mating seated reception into the single associated one of the sockets 74. The outer cap 96 additionally includes a secondary inner thread segment 100 for threaded assembly with an inner cap 102 of generally cup-shaped geometry to define cooperatively a metering chamber 104 of predetermined known volume. A cylindrical shuttle valve 106 having a closed lower end (FIGS. 11–12) is movably carried between the outer and inner caps 96 and 102, guided by guide posts 108 (FIG. 9) and biased by a spring 110 toward a normal lower position engaging an annular valve seat 112 on the outer cap 96 to close a dispense port 114 formed therein. A seal ring 116 is shown at the lower end of the shuttle valve 106 for engaging and sealing against the valve seat 112.

Figure 11:
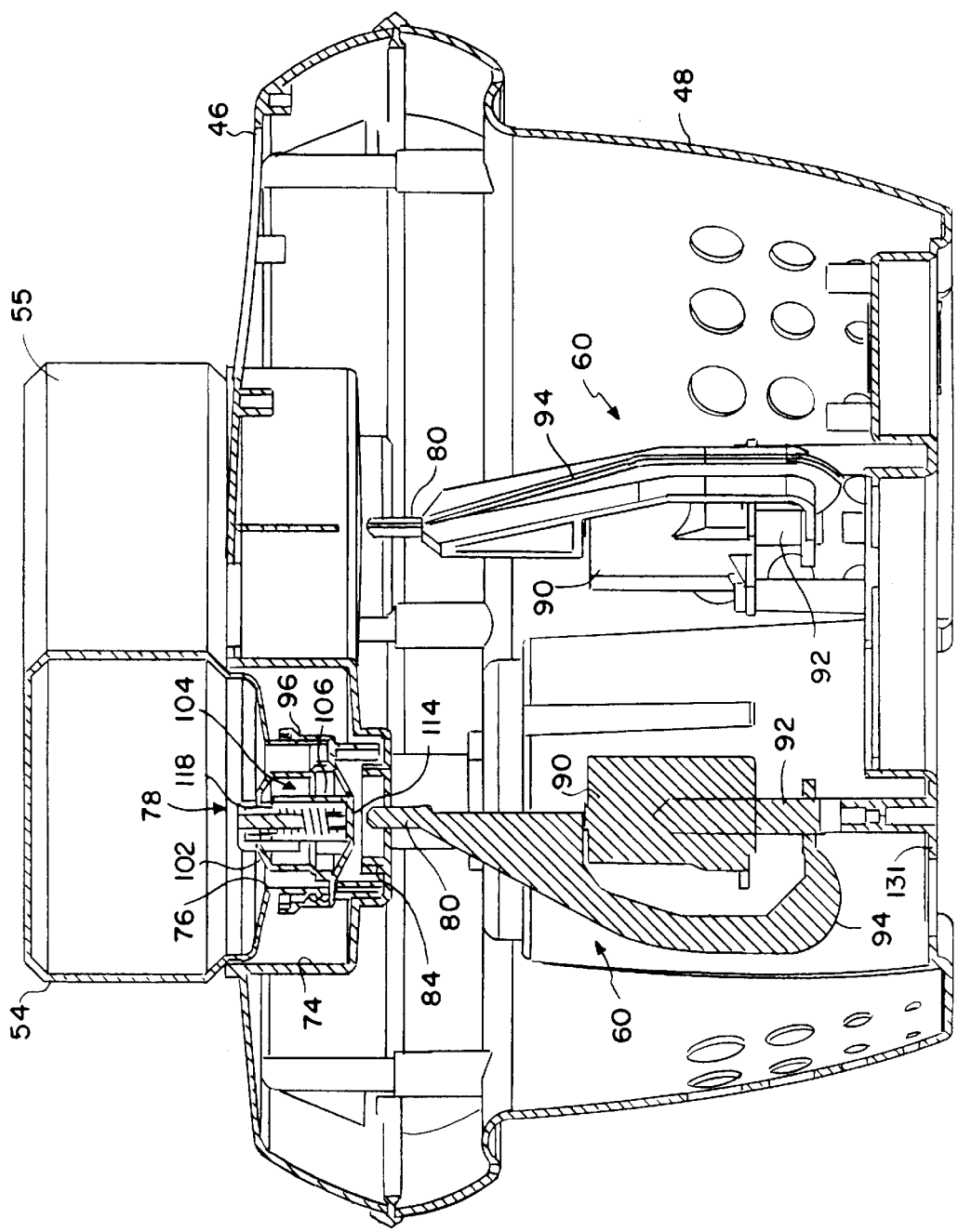
FIG. 11 is an enlarged fragmented vertical sectional view taken generally on the line 11—11 of FIG. 2, showing the metering assembly in a normal closed position.
Figure 12:
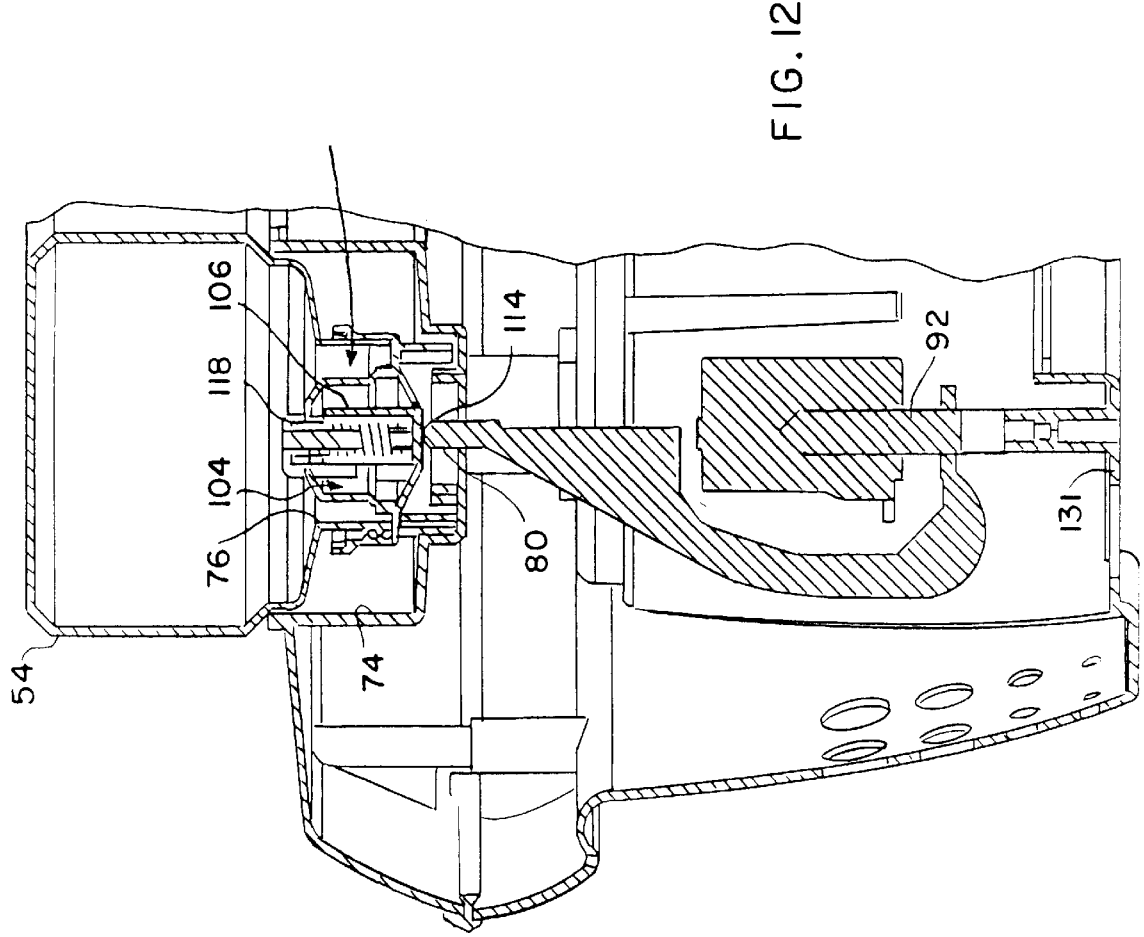
FIG. 12 is an enlarged fragmented vertical sectional view similar to a portion of FIG. 11, but illustrating metering assembly engagement with a solenoid actuator mounted within the unit housing, with the solenoid actuator in an advanced position for dispensing a chemical agent from the container.

In this normal spring-loaded lower position, as viewed in FIG. 11, an upper margin of the shuttle valve 106 is spaced downwardly below a metering port 118 formed in the inner cap 102, to permit flow of the liquid chemical agent within the bottle 54 downwardly from the hollow bottle interior to fill the metering chamber 104. In this regard, an open web 120 is shown installed within this metering port 118, to include a central post 122 for supporting and retaining an upper end of the spring 110 which extends downwardly into and applies the normal downward biasing force to the shuttle valve 106.

When the associated solenoid actuator 60 is activated by the controller 16 to dispense the chemical agent within the bottle 54, the plunger tip 80 is advanced upwardly within the socket 74 to engage the closed lower end of the shuttle valve 106. The plunger tip 80 moves the shuttle valve 106 through an upward stroke to an upper position within the metering chamber 104, as viewed in FIG. 12. In this upper position, the upper margin of the shuttle valve 106 is moved against the inner cap 102 in surrounding relation to the metering port 118 to isolate the metering chamber 1 18 from the bottle interior. At the same time, however, the lower closed end of the shuttle valve 106 is also moved upwardly from the valve seat 112 to permit chemical agent within the metering chamber 118 to flow downwardly through the dispense port 114. The chemical agent thus exits the bottle for further flow downwardly through the central port 82 in the socket 74 (FIG. 6) to mix with the spa water 14 which substantially fills the lower housing base 48 when the monitor unit 10 is floated within the spa. Subsequent retraction of the plunger tip 80 enables the shuttle valve 106 to shift back to the lowered position as viewed in FIG. 11, whereupon the metering chamber 118 is allowed to re-fill with a second metered volume dose of the chemical agent. For any given dispense cycle, the controller 16 operates the solenoid actuator 60 to advance and retract the plunger tip 80 through a number of strokes sufficient to dispense an appropriate quantity of the chemical agent to the spa water. Importantly, in the event of failure of the associated solenoid actuator 60 for any reason or at any time, the use of the metering assembly 58 insures that the interior of the chemical-containing bottle is not open for direct and complete drainage dispensing of the entire bottle contents to the spa water.

Figure 13:
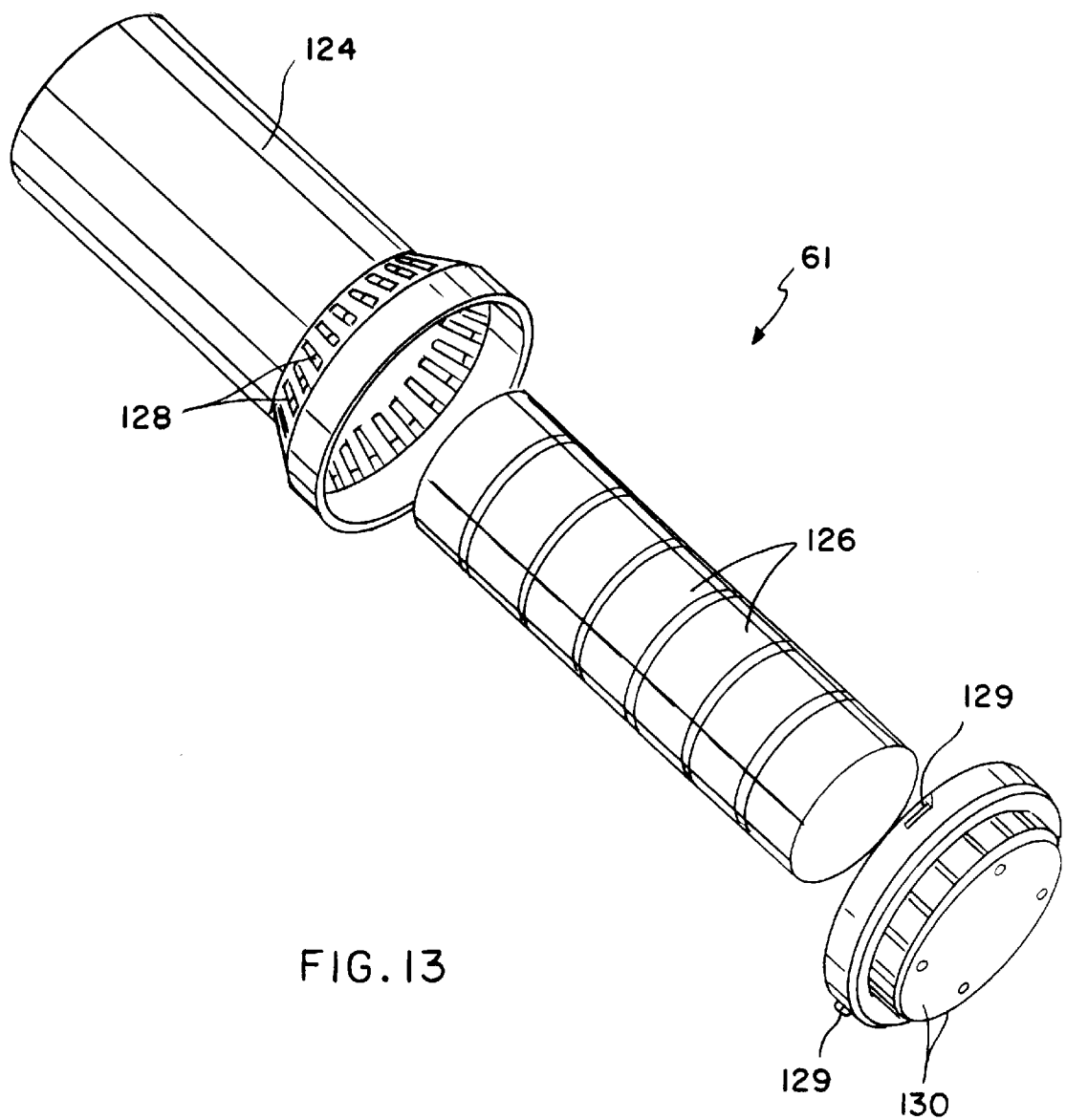
FIG. 13 is an exploded perspective view showing an alternative chemical agent container in the form of a cartridge for supporting a supply of soluble tablets.
Figure 14:
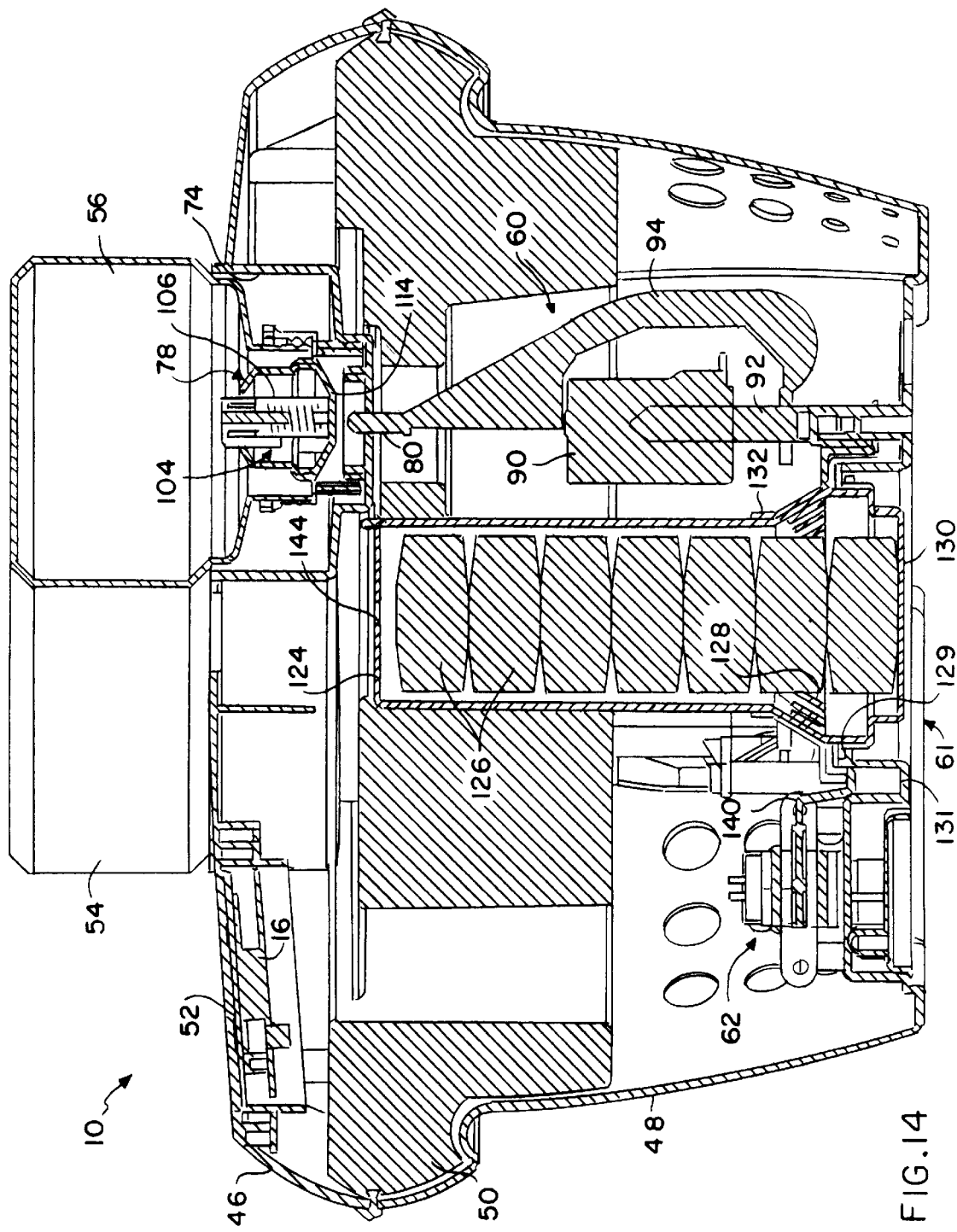
FIG. 14 is an enlarged fragmented vertical sectional view of a portion of the monitor unit, depicting installation of the soluble tablet cartridge into the monitor unit.

The cartridge 61 containing the soluble chemical sanitizing agent such as bromine in tablet form is shown in FIG. 13. As shown, this cartridge 61 conveniently comprises a compact cylindrical cartridge housing 124 adapted to be pre-loaded or pre-packaged with a stack of soluble tablets 126. A lower end of this cartridge housing 124 is flared outwardly with a truncated conical shape which has a circumferential array of perforations 128 formed therein. A lower cap 130 is attached to and closes the lower end of the cartridge housing, wherein this cap 130 is shown bearing the Roman numeral designation "IV".

Figure 15:
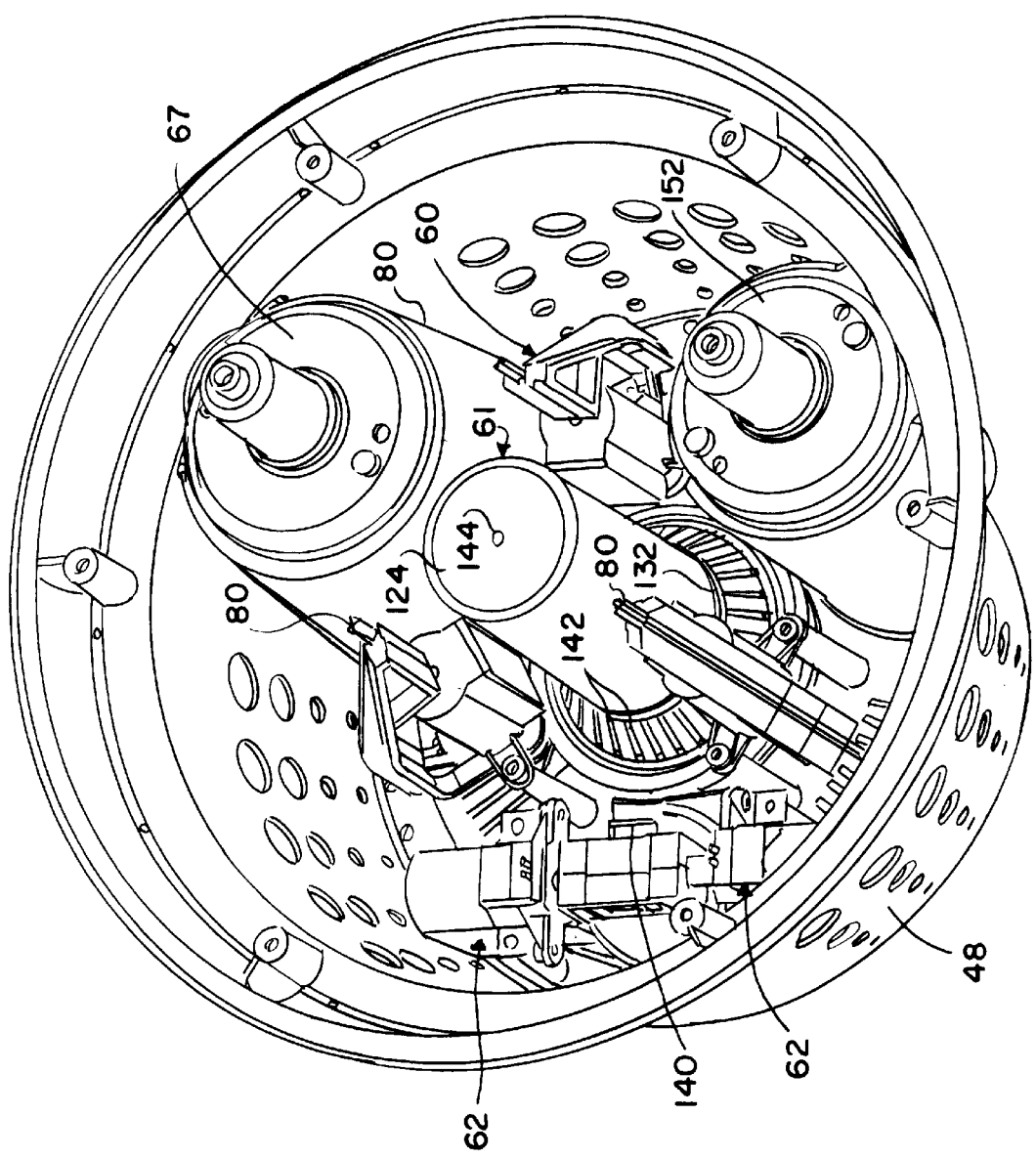
FIG. 15 is a perspective view similar to FIG. 7, and illustrating a movable gate in an open position for dissolution of the soluble tablets to dispense a chemical agent carried thereby to the spa water.

The cartridge 61 is sized and shaped for quick and easy mounting into a central opening formed in a bottom wall 131 within the lower housing base 48, as viewed in FIG. 15. In this regard, the cartridge 61 may include radially outwardly projecting ears 129 on the lower cap 130 for suitable partturn, quick-connect and quick-release attachment to the wall 131 of the housing base. When installed, the perforate segment 128 of the cartridge is positioned within a rotary gate 132 of truncated conical shape and mounted on the housing base 48 for back and forth rotation through a short arcuate or part-circumferential stroke, on the order of about 5–6 degrees. Such back and forth displacement of the rotary gate 132 is achieved by a push-pull action from the set of solenoid actuators 62 mounted on the housing base 48 by means of a pair of brackets 134. These solenoid actuators 62 each include a plunger 136 (shown best in FIG. 5) protruding from an associated armature 138 for engaging opposite sides of a radially outwardly extending bearing lug 140 on the rotary gate 132. Importantly, the rotary gate 132 has a generally truncated conical shape to closely overlie the perforated flared portion of the cartridge 61, and the gate 132 also includes a circumferential array of perforations 142. Back and forth positional adjustment of the rotary gate 132 thus effectively opens (FIG. 7) or closes (FIG. 15) the perforations 128 in the cartridge housing 124, by respective alignment or misalignment of the gate perforations 142 therewith, to correspondingly regulate water contact with and the resultant dissolution rate of the soluble tablets 126, all in response to operation of the solenoid actuators 62 under control by the controller 16.

In the preferred form, with the soluble tablets 126 containing a bromine sanitizing agent for regulating spa water ORP level, the controller 16 may be programmed to take and ORP reading at relatively frequent intervals of about three hours. In response to the ORP reading as detected by the controller 16, the controller 16 then operates the solenoid actuators 62 to displace the rotary gate 132 in a manner opening the perforations 128 in the cartridge housing 124 if the ORP level is below a target range, typically a low voltage reading on the order of about 650–750 millivolts when the pH level is within the prescribed range. Alternately, if the ORP reading is within or above this target range, which may be programmed into the controller 16, the solenoid actuators 62 displace the rotary gate 132 in a manner closing the perforations 128 in the cartridge housing 124. Alternately, if desired, the controller 16 can be programmed to modulate the degree to which the cartridge housing perforations 128 are opened, in accordance with the ORP reading.

The tablet-containing cartridge 61 may optionally be equipped with a small viewing port 144 (FIGS. 7 and 15) formed in the upper end thereof, for alignment with a related site port 148 (FIG. 2) formed in the upper housing plate 46. With this geometry, the interior of the cartridge 61 can be visually monitored to determine when the tablets 126 therein have dissolved, thereby requiring installation of a replacement cartridge. Such visual monitoring can be enhanced by forming the cap 130 at the lower end of the cartridge 61 from a translucent material or the like, whereupon light can be perceived when viewing through the site port 148 only in the event that the tablets 126 have been dissolved.

FIG. 5 shows a sensor unit 150 mounted within the lower housing base 48, as by removable connection into the underside of a mounting fixture 152. The sensor unit 150 carries the pair of sensor electrodes 18 and 20 in electrical communication with the controller 16 which activates the electrodes 18 and 20 at programmed times to take water parameter readings such as the pH and ORP readings described above. The sensor electrodes 18 and 20 are positioned within a moisture cup 154 carried as by snap-fit mounting on the lower end of the unit 150, to capture and retain a quantity of water therein when the monitor unit 10 is removed temporarily from the spa during spa use. Maintaining the sensor electrodes 18 and 20 immersed or in contact with the water has been found to effectively prevent electrode corrosion and degradation which could otherwise shorten operating life. A third electrode comprising the water sensor 72, such as a conductivity probe, may also be carried by the sensor unit 150 in a position out of contact with water contained within the moisture cup 154, to signal the controller 16 when the monitor unit 10 is removed from the spa, so that water chemistry readings and responsive dispensing of chemical agents does not occur until the monitor unit 10 is returned to the spa.

The spa chemistry monitor unit 10 of the present invention thus provides a relatively compact and self-contained, free floating device for automatically monitoring the quality of the spa water 14. The monitor unit is programmed to take water chemistry readings at regular intervals, and to respond in an unattended manner by dispensing appropriate chemical agents in the appropriate dosages to maintain water clarity and hygiene.

A variety of modifications and improvements in and to the spa chemistry monitor unit will be apparent to those persons skilled in the art. As one example, it will be recognized and understood that the monitor unit may be utilized for larger bodies of water, such as a swimming pool, wherein the chemical-carrying capacity would desirably be increased to accommodate the larger water volume. Moreover, it will be understood that the monitor unit 10 can be adapted to carry additional or alternative chemical agents, such as a flocculent-type water clarifier and others. In one form, the clarifier may be combined with another chemical agent, such as the acid solution for decreasing the pH level. Other agents such as a selected fragrance may also be dispensed automatically or manually by the monitor unit. Accordingly, no limitation on the invention is intended by way of the foregoing description and accompanying drawings, except as set forth in the append claims.

What is claimed is:

1. A water chemistry monitor unit, comprising:
   a buoyant housing adapted for free floating placement into a body of water within a spa tub;
   at least one sensor electrode carried by said housing;
   a controller for periodically activating said at least one sensor electrode to take a selected water chemistry reading at predetermined time intervals;
   at least one chemical agent carried by said housing, said at least one chemical agent comprising a plurality of liquid agents respectively within a plurality of bottles each having a bottle neck, said housing including a plurality of upwardly open sockets for respectively and removably supporting said bottle necks of said bottles with said bottles in an inverted orientation, and further wherein said bottles necks and said sockets each include cooperative means for respective and complementary mating fit of each of said bottle necks with a single one of said sockets in accordance with the specific chemical agent carried by each of said bottles; and
   dispense means operated by said controller to dispense said at least one chemical agent to the water in an amount responsive to said water chemistry reading.

2. The water chemistry monitor unit of claim 1 wherein said at least one sensor electrode comprises a plurality of sensor electrodes, said controller respectively activating said plurality of sensor electrodes to take a plurality of selected water chemistry readings at predetermined time intervals, said dispense means being operated by said controller to dispense said each of said plurality of chemical agents to the water in amounts responsive to said plurality of water chemistry readings.

3. The water chemistry monitor unit of claim 1 further including a buoyant float ring carried by said housing.

4. The water chemistry monitor unit of claim 1 further including data entry means carried by said housing for programming said controller to take water chemistry readings at selected times.

5. The water chemistry monitor unit of claim 1 further including battery power means carried by said housing.

6. The water chemistry monitor unit of claim 1 further including means for detecting removal of said housing from the water, said controller being responsive to said removal detecting means to interrupt water chemistry readings and chemical agent dispensing until said housing is returned to the water.

7. The water chemistry monitor unit of claim 1 further including means for maintaining said at least one sensor electrode immersed within water upon removal of said housing from the water.

8. The water chemistry monitor unit of claim 1 further including a metering assembly mounted within each of said bottle necks, each of said metering assemblies including reciprocal valve means movable back and forth within a metering chamber of predetermined volumetric size, said dispense means comprising a plurality of reciprocal plunger tips carried by said housing respectively within said sockets for engaging said valve means of said metering assemblies to dispense a metered dose of the chemical agent from each of said bottles.

9. The water chemistry monitor unit of claim 8 wherein said dispense means further includes a plurality of solenoid actuators for respectively advancing and retracting said plunger tips.

10. The water chemistry monitor unit of claim 1 wherein said at least one chemical agent further comprises a plurality of soluble tablets carried within a cartridge removably mounted on said housing, said cartridge including a perforated segment, and said dispense means including a movable perforated gate carried by said housing in overlying relation to said perforated cartridge segment and movable back and forth to open and close said perforated cartridge segment.

11. The water chemistry monitor unit of claim 10 further including site means for visually siting through said cartridge to determine when said cartridge is empty.

12. The water chemistry monitor unit of claim 11 wherein said site means comprises an open viewing port formed at an upper end of said cartridge when said cartridge is installed on said housing, and a translucent cap at a lower end of said cartridge.

13. The water chemistry monitor unit of claim 10 wherein said dispense means further includes at least one solenoid actuator for movably positioning said movable gate relative to said perforated cartridge segment.

14. The water chemistry monitor unit of claim 1 wherein said at least one sensor electrode comprises a pH sensor for taking a reading of water pH level, and an oxygen reduction potential (ORP) sensor for taking a reading of water ORP level.

15. A water chemistry monitor unit, comprising:
   a buoyant housing adapted for free floating placement into a body of water within a spa tub;
   a first sensor electrode carried by said housing for contacting the water upon placement of said housing into the body of water, said first sensor electrode being adapted to measure water pH level;
   a second sensor electrode carried by said housing for contacting the water upon placement of said housing into the body of water, said second sensor electrode being adapted to measure water oxygen reduction potential (ORP);
   a controller carried by said housing for periodically activating said first and second sensor electrodes to take water pH level and ORP level readings in accordance with a programmed schedule;
   a first chemical agent carried by said housing for increasing water pH level when added to the water;
   a second chemical agent carried by said housing for decreasing water pH level when added to the water;
   said first and second chemical agents each comprising a liquid agent contained respectively within a pair of bottles each having a bottle neck, said housing including mounting means for removably supporting said bottles in an inverted orientation, said mounting means comprising a pair of upwardly open sockets for respectively and removably supporting said bottle necks of said pair of bottles, and further wherein said bottle necks and said sockets each include cooperative means for respective and unique mating fit of each of said bottle necks with a single one of said sockets in accordance with the specific chemical agent carried by each of said bottles;

a third chemical agent carried by said housing for increasing water ORP level when added to the water; and dispense means operated by said controller in response to a water pH level reading to dispense a selected one of said first and second chemical agents to the water in an amount responsive to the water pH level reading;

said dispense means being further operated by said controller in response to a water ORP level reading to control dispensing of said third chemical agent to the water.

16. The water chemistry monitor unit of claim 15 further including means carried by said housing for programming said controller to take water pH level and water ORP level readings at selected times.

17. The water chemistry monitor unit of claim 15 further including battery power means carried by said housing.

18. The water chemistry monitor unit of claim 15 further including means for detecting removal of said housing from the water, said controller being responsive to said removal detecting means to interrupt water pH and ORP level readings and chemical agent dispensing until said housing is returned to the water.

19. The water chemistry monitor unit of claim 15 further including means for maintaining said first and second sensor electrodes immersed within water upon removal of said housing from the water.

20. The water chemistry monitor unit of claim 19 wherein said means for maintaining said first and second electrodes immersed within water upon removal of said housing from the water comprises a moisture cup for retaining a quantity of water therein upon removal of said housing from the water, said first and second electrodes protruding into said moisture cup.

21. The water chemistry monitor unit of claim 15 further including a metering assembly mounted within each of said bottle necks, said metering assemblies each including reciprocal valve means movable back and forth within a metering chamber of predetermined volumetric size, said dispense means comprising a pair of reciprocal plunger tips carried by said housing for respectively engaging said valve means to dispense a metered dose of the chemical agent from each of said bottles.

22. The water chemistry monitor unit of claim 21 wherein said dispense means further includes a pair of solenoid actuators for respectively advancing and retracting said pair of plunger tips.

23. The water chemistry monitor unit of claim 15 wherein said third chemical agent comprises a plurality of soluble tablets carried within a cartridge removably mounted on said housing, said cartridge including a perforated segment, and said dispense means including a movable perforated gate carried by said housing in overlying relation to said perforated cartridge segment and movable back and forth to open and close said perforated cartridge segment.

24. The water chemistry monitor unit of claim 23 wherein said dispense means further includes at least one solenoid actuator for movably positioning said movable gate relative to said perforated cartridge segment.

25. The water chemistry monitor unit of claim 15 further including a fourth chemical agent carried by said housing, said dispense means being operated by said controller to dispense said fourth chemical agent to the water.

26. A water chemistry monitor unit, comprising:

a buoyant housing adapted for placement into a body of water within a spa tub;

a plurality of sensor electrodes carried by said housing in a position immersed within the water when said housing is placed into the water, said sensor electrodes being adapted to take water chemistry readings;

a controller carried by said housing for periodically activating said sensor electrodes to take water chemistry readings;

means carried by said housing for programming said controller to take specific water chemistry readings in accordance with a programmed schedule;

a plurality of bottles each having a respective chemical agent contained therein, each of said bottles having a bottle neck;

a plurality of sockets formed on said housing for respectively receiving the necks of said bottles to removably support said bottles on said housing in a generally inverted orientation, each of said bottles and a corresponding unique one of said sockets including complementary interfit means to prevent mounting thereof into a different one of said sockets; and dispense means operated by said controller to dispense the chemical agents from said bottles to the water.

27. The water chemistry monitor unit of claim 26 further including a cartridge removably mounted on said housing and loaded with a plurality of soluble tablets carrying a selected chemical agent, said cartridge including a perforated segment, and said dispense means further including a movable perforated gate carried by said housing in overlying relation to said perforated cartridge segment and movable back and forth to open and close said perforated cartridge segment.

28. The water chemistry monitor unit of claim 27 wherein said dispense means further includes at least one solenoid actuator for movably positioning said movable gate relative to said perforated cartridge segment.

29. The water chemistry monitor unit of claim 26 further including battery power means carried by said housing.

30. The water chemistry monitor unit of claim 26 further including means for detecting removal of said housing from the water, said controller being responsive to said removal detecting means to interrupt water chemistry readings and chemical agent dispensing until said housing is returned to the water.

31. The water chemistry monitor unit of claim 26 further including means for maintaining said sensor electrodes immersed within water upon removal of said housing from the water.

32. The water chemistry monitor unit of claim 26 further including a metering assembly mounted within each of said bottle necks, said metering assemblies each including reciprocal valve means movable back and forth within a metering chamber of predetermined volumetric size, said dispense means comprising a plurality of reciprocal plunger tips carried by said housing for respectively engaging said valve means to dispense a metered dose of the chemical agent from each of said bottles.

33. The water chemistry monitor unit of claim 32 wherein said dispense means further includes a plurality of solenoid actuators for respectively advancing and retracting said plurality of plunger tips.

* * * * *